US011465791B2

(12) United States Patent
Watkinson et al.

(10) Patent No.: US 11,465,791 B2
(45) Date of Patent: Oct. 11, 2022

(54) PROPELLANT CONDITIONING ASSEMBLIES

(71) Applicant: MEXICHEM FLUOR S.A. DE C.V., San Luis Potosi (MX)

(72) Inventors: Paul Anthony Watkinson, Chester (GB); Paul Alan Dowdle, St. Helens Merseyside (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 378 days.

(21) Appl. No.: 16/603,718

(22) PCT Filed: Mar. 21, 2018

(86) PCT No.: PCT/GB2018/050740
§ 371 (c)(1),
(2) Date: Oct. 8, 2019

(87) PCT Pub. No.: WO2018/197829
PCT Pub. Date: Nov. 1, 2018

(65) Prior Publication Data
US 2020/0130875 A1 Apr. 30, 2020

(30) Foreign Application Priority Data

Apr. 28, 2017 (GB) .................................. 1706785

(51) Int. Cl.
*B65B 31/00* (2006.01)
*A61M 15/00* (2006.01)
*B01J 4/00* (2006.01)

(52) U.S. Cl.
CPC ....... *B65B 31/003* (2013.01); *A61M 15/0028* (2013.01); *B01J 4/008* (2013.01); *A61M 2205/3334* (2013.01); *A61M 2205/3368* (2013.01); *A61M 2205/36* (2013.01); *A61M 2205/3606* (2013.01); *A61M 2209/045* (2013.01); *B01J 2204/007* (2013.01)

(58) Field of Classification Search
CPC ............. B65B 31/003; A61M 15/0028; A61M 2205/3334; A61M 2205/3368; A61M 2205/36; A61M 2205/3606; A61M 2209/045; B01J 2204/007
USPC .......................................................... 141/20
See application file for complete search history.

(56) References Cited

U.S. PATENT DOCUMENTS 4,705,082 A * 11/1987 Fanshawe ............. B65B 31/003
141/82
4,909,038 A 3/1990 Porter
(Continued)

FOREIGN PATENT DOCUMENTS

CN 101943082 1/2011
CN 102211003 A 10/2011
(Continued)

OTHER PUBLICATIONS

Liptak, "Heat Exchanger Control and Optimization"; 8.29, Instrument Engineers' Handbook—Process Control and Optimization, Jan. 30, 2006, Taylor & Francis Group, vol. II, pp. 2004-2024, Multipurpose Systems p. 2022, 2021, Figure 8.29kk.
(Continued)

*Primary Examiner* — Jason K Niesz
(74) *Attorney, Agent, or Firm* — Crowell & Moring LLP

(57) ABSTRACT

In the field of medical dosing device filling, a propellant conditioning assembly (10) comprises an input conduit (12) to receive a propellant at a constant pressure from a propellant reservoir (102). The conditioning assembly (10) also includes a bifurcation (18) to divide the input conduit (12) into first and second conditioning conduits (20, 22). The first conditioning conduit (20) includes a cooler device (24) to selectively cool a diverted first propellant stream (26) that flows through the first conditioning conduit (20), and the second conditioning conduit (22) includes a heater device (32) to selectively heat a diverted second propellant stream (34) that flows through the second conditioning conduit
(Continued)

(22). The conditioning assembly (10) still further includes an output conduit (44) to receive the first and second propellant streams (26, 34). The relative proportion of the first and second propellant streams (26, 34) merging in the output conduit (44) is controlled to regulate the temperature of a merged constant pressure propellant feed (46) exiting from the output conduit (44).

8 Claims, 2 Drawing Sheets

(56) References Cited

U.S. PATENT DOCUMENTS

| | | |
|---|---|---|
| 6,968,673 B1 | 11/2005 | Knight |
| 2006/0086100 A1 | 4/2006 | Taube |
| 2014/0130522 A1 | 5/2014 | Steffen et al. |

FOREIGN PATENT DOCUMENTS

| | | |
|---|---|---|
| CN | 104014294 A | 9/2014 |
| CN | 104028189 A | 9/2014 |
| JP | 2000248994 | 9/2000 |
| KR | 101211395 B1 | 12/2012 |

OTHER PUBLICATIONS

Figure 1:
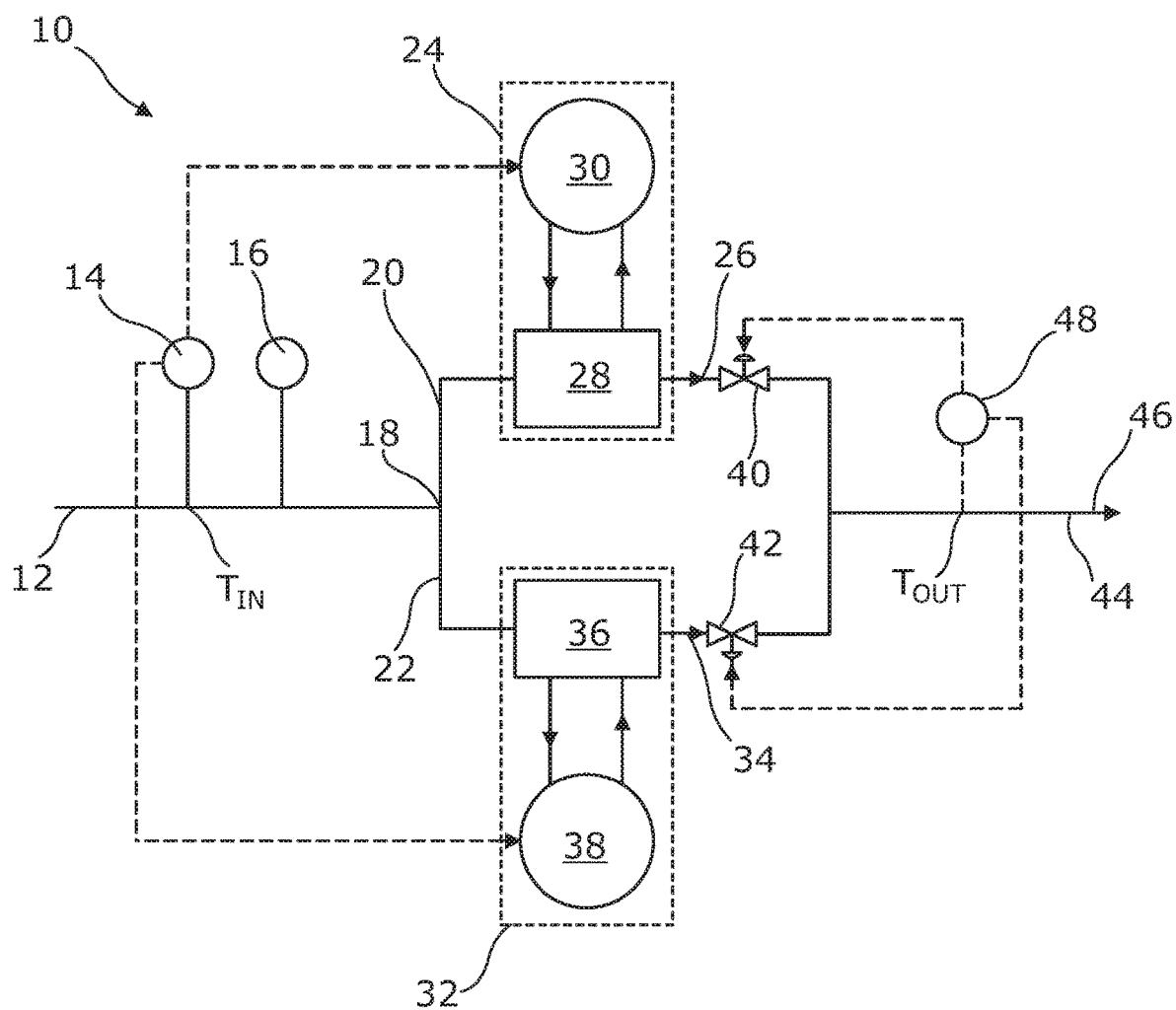

McMillan, "How to Make Transitions Between Cooling and Heating Smooth and Fast", online, Jul. 15, 2015, url:http://automation.isa.org/2015/07/how-to-make-transitions-between-cooling-and-heating-smooth-and-fast/ Figure 1.

Search Report for 201880027237.5, dated Jun. 9, 2021, 3 pp.

Instrument Engineers' Handbook, $4^{th}$ Edition "Process Control and Optimization," vol. II, Jan. 30, 2006, pp. 2004-2024.

Search Report dated Oct. 31, 2017 from corresponding Great Britain Application No. GB1706785.1.

International Search Report dated May 30, 2018 from corresponding International Application Serial No. PCT/GB2018/050740.

* cited by examiner

PROPELLANT CONDITIONING ASSEMBLIES

This application is a U.S. National Phase entry under 35 U.S.C. § 371 of International application No. PCT/GB2018/050740, filed Mar. 21, 2018, which claims the benefit of Great Britain patent application No. 1706785.1, filed Apr. 28, 2017, the contents of each of which are incorporated herein by reference in their entireties.

This invention relates to a propellant conditioning assembly, a process plant including such an assembly, and a method of conditioning a propellant.

Drugs for treating illnesses such as respiratory disorders are frequently administered in aerosol formulations. Such aerosol drug formulations are typically delivered using a medical dosing device, e.g. a Metered Dose Inhaler (MDI), which contains the drug formulation along with a propellant. A nozzle or similar atomising outlet included within the dosing device is operated, e.g. depressed, to deliver the medication in an atomised form.

Example propellants for medical dosing devices include hydrofluorocarbons (HFCs) such as HFC 134a (1,1,1,2-tetrafluoroethane), HFC 227ea (1,1,1,2,3,3,3-heptafluoropropane) and HFC 152a (1,1-difluoroethane).

Conditioning a propellant, i.e. stabilising its liquid density by providing it at a constant pressure and temperature, is often essential prior to filling a dosing device with the propellant, especially when performing a dual fill of a dosing device with a concentrated drug suspension being added to the device prior to the propellant.

According to a first aspect of the invention there is provided a propellant conditioning assembly, for providing a propellant feed to a medical dosing device filling apparatus, the assembly comprising:
- an input conduit to receive a propellant at a constant pressure from a propellant reservoir;
- a bifurcation to divide the input conduit into first and second conditioning conduits, the first conditioning conduit including a cooler device to selectively cool a diverted first propellant stream flowing through the first conditioning conduit, and the second conditioning conduit including a heater device to selectively heat a diverted second propellant stream flowing through the second conditioning conduit; and
- an output conduit to receive the first and second propellant streams, the relative proportion of the first and second propellant streams merging in the output conduit being controlled to regulate the temperature of a merged constant pressure propellant feed exiting from the output conduit.

The ability to regulate the temperature of a constant pressure propellant feed exiting from an output conduit, i.e. the ability to condition the propellant in the foregoing manner is advantageous because it permits the continuous, inline conditioning of a propellant in real time. As a result, conditioned propellant is readily and consistently available, e.g. for a downstream medical dosing device filling apparatus, and there is no requirement to store large quantities of conditioned propellant.

This latter benefit is especially important with respect to flammable hydrofluorocarbon (HFC) propellants, such as HFC 152a (1,1-difluoroethane), as it avoids the associated fire and safety hazards.

Preferably the input conduit includes an input temperature sensor arranged to measure an input temperature of the propellant in the input conduit, the measured input temperature being used to control the selective operation of the cooler and heater devices.

The inclusion of such an input temperature sensor introduces a degree of feedback control to the propellant conditioning assembly of the invention, and allows relatively coarse changes to be made to the temperature of the respective propellant streams, which in turn allows for finer, subsequent regulation of the temperature of the merged propellant feed in the output conduit.

Optionally the cooler device is operated to cool the first propellant stream flowing through the first conditioning conduit when the measured input temperature is greater than a first temperature threshold.

Such an arrangement desirably cools the first propellant stream when the temperature of the propellant in the input conduit is higher than desired, and therefore makes available a cooled propellant stream for downstream merging in the output conduit with the second propellant stream.

The heater device may be operated to heat the second propellant stream flowing through the second conditioning conduit when the measured input temperature is less than a second temperature threshold.

Such an arrangement desirably heats the second propellant stream when the temperature of the propellant in the input conduit is lower than desired, and therefore makes available a heated propellant stream for downstream merging in the output conduit with the first propellant stream.

In a preferred embodiment of the invention the first and second temperature thresholds differ from one another.

Having differing first and second temperature thresholds helps to reduce the need to operate the cooler and heater devices, i.e. by causing one or other of them to operate only when the input temperature is outside the temperature range defined by the said first and second thresholds.

Preferably each of the cooler device and the heater device is or includes a heat exchanger.

Heat exchangers are able efficiently to remove or add heat to a respective propellant stream in a controlled and safe manner.

Optionally the first conditioning conduit includes a first flow control valve to control the flow rate through the first conditioning conduit and the second conditioning conduit includes a second flow control valve to control the flow rate through the second conditioning conduit.

The inclusion of such flow control valves permits the ready and effective control of the flow rate through each conditioning conduit, and hence helps also to control the relative proportion of first and second propellant streams that merge in the output conduit.

In another preferred embodiment of the invention the output conduit includes an output temperature sensor arranged to measure an output temperature of the merged constant pressure propellant feed in the output conduit, the measured output temperature being used to control the operation of the first and second flow control valves.

The inclusion of such an output temperature sensor introduces a further degree of feedback control to the propellant conditioning assembly of the invention and assists, via control of the first and second control valves, with close regulation of the temperature of the merged propellant feed in the output conduit.

In a still further preferred embodiment of the invention the first flow control valve is operated to increase the flow rate through the first conditioning conduit and/or the second flow control valve is operated to reduce the flow rate through the second conditioning conduit when the measured output temperature is above a first output threshold, and the first flow control valve is operated to reduce the flow rate through the first conditioning conduit and/or the second flow control valve is operated to increase the flow rate through the second conditioning conduit when the measured output temperature is below a second output threshold.

Such an arrangement permits fine control over the relative proportions of different temperature first and second propellant streams that merge in the output conduit, and hence similarly fine regulation of the temperature of the merged constant pressure propellant feed in the output conduit.

The input conduit may include an input flow rate sensor to measure the flow rate of the propellant through the input conduit.

The inclusion of such a flow rate sensor assists with controlling the relative proportion of first and second propellant streams that merge in the output conduit.

According to a second aspect of the invention there is provided a process plant, for providing a propellant feed to a medical device filling apparatus, comprising a propellant reservoir for a quantity of propellant and a supply line extending from the reservoir to a propellant conditioning assembly as described hereinabove, the supply line including a constant pressure pump to supply propellant at a constant pressure to the propellant conditioning assembly.

The process plant shares the benefits associated with the propellant conditioning assembly mentioned hereinabove.

According to a third aspect of the invention there is provided a method of conditioning a propellant, for feeding to a medical dosing device filling apparatus, comprising the steps of:

(a) receiving in an input conduit a propellant at a constant pressure from a propellant reservoir;
(b) dividing the input conduit into first and second conditioning conduits, the first conditioning conduit including a cooler device to selectively cool a diverted first propellant stream flowing through the first conditioning conduit, and the second conditioning conduit including a heater device to selectively heat a diverted second propellant stream flowing through the second conditioning conduit;
(c) receiving the first and second propellant streams in an output conduit; and
(d) controlling the relative proportion of the first and second propellant streams merging in the output conduit to regulate the temperature of a merged constant pressure propellant feed exiting from the output conduit.

The method of the invention similarly shares the benefits of the corresponding features of the propellant conditioning assembly of the invention.

Figure 2:
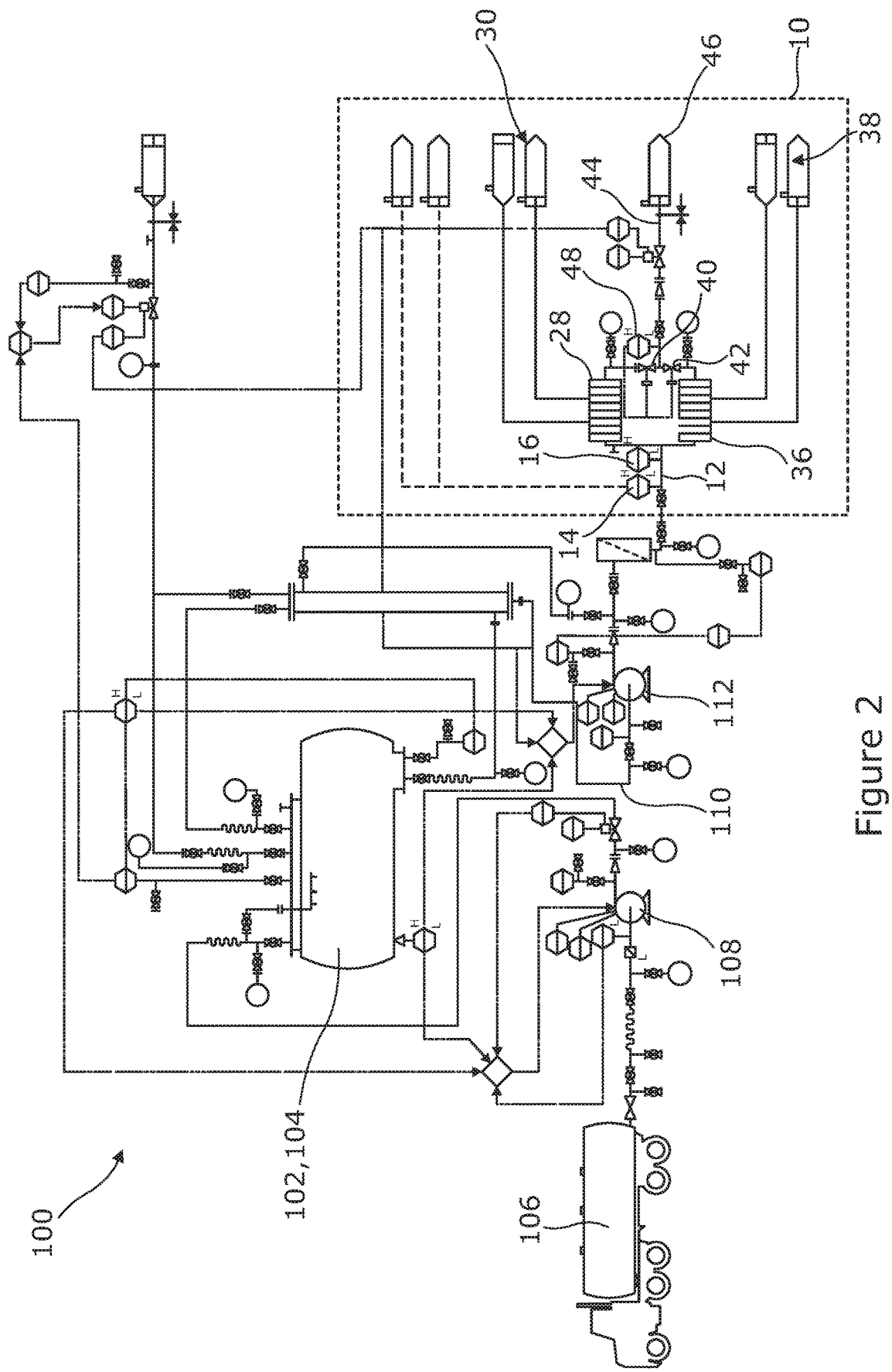

There now follows a description of preferred embodiments of the invention, by way of non-limiting example, with reference being made to the following figures in which:

FIG. 1 shows a schematic view of a propellant conditioning assembly according to a first embodiment of the invention; and FIG. 2 shows a schematic view of a process plant according to a further embodiment of the invention within which is located the propellant conditioning assembly shown in FIG. 1.

A propellant conditioning assembly according to a first embodiment of the invention is designated generally by reference numeral 10, as shown in FIG. 1.

The propellant conditioning assembly 10 includes an input conduit 12 which, in use, receives a propellant at a constant pressure from a propellant reservoir (not shown in FIG. 1).

The input conduit 12 includes an input temperature sensor 14 that is arranged to measure an input temperature $T_{IN}$ of the propellant in the input conduit 12, and an input flow rate sensor 16 to measure the flow rate of the said propellant. The input flow rate sensor 16 preferably includes high and low flow rate alarms, e.g. to alert an operative to potential malfunction of the propellant conditioning assembly 10.

The propellant conditioning assembly 10 also includes a bifurcation 18 that divides the input conduit 12 into first and second conditioning conduits 20, 22.

The first conditioning conduit 20 includes a cooler device 24 to selectively cool a diverted first propellant stream 26 which flows through the first conditioning conduit 20.

More particularly, the cooler device 24 includes a first heat exchanger 28 that is arranged in communication with a cooler module 30 which supplies a cooled fluid to the first heat exchanger 28 to remove heat, i.e. cool, the first propellant stream 26 as it passes through the first conditioning conduit 20. Preferably the first heat exchanger 28 is a plate heat exchanger, and more preferably still a stainless steel welded plate heat exchanger, although other types of heat exchanger may also be used.

In the embodiment shown the cooler module 30 receives cooled fluid in the form of chilled water from a dedicated water chiller (not shown) that operates at a reduced temperature set and monitored by a high-level controller, e.g. located elsewhere within a process plant of which the propellant conditioning assembly 10 forms a part. Other cooled fluids may be used however, as may other ways of cooling the first heat exchanger 28.

Meanwhile, the second conditioning conduit 22 includes a heater device 32 to selectively heat a diverted second propellant stream 34 which flows through the second conditioning conduit 22.

The heater device 32 includes a second heat exchanger 36 that is arranged in communication with a heater module 38 which supplies a heated fluid to the second heat exchanger 36 to transfer warmth to, and thereby heat, the second propellant stream 34 as it passes through the second conditioning conduit 22. Preferably the second heat exchanger 36 is again a plate heat exchanger, and more preferably still a stainless steel welded plate heat exchanger, although other types of heat exchanger may again also be used.

In the embodiment shown the heater module 38 receives heated fluid in the form of hot water from a dedicated water heater (not shown) that operates at an elevated temperature, which may similarly be set and monitored by a high-level controller located elsewhere within a process plant of which the propellant conditioning assembly 10 forms a part. Preferably the heater module 38 includes a safety device (not shown) to prevent overheating of the hot water. Other heated fluids may be used however, as may other ways of heating the second heat exchanger 36. A self-acting float valve (also not shown) ensures that the water heater is provided with fresh water, as needed.

In addition to the foregoing, the first conditioning conduit 20 includes a first flow control valve 40 to control the flow rate of the first propellant stream 26 through the first conditioning conduit 20. Also, the second conditioning conduit 22 includes a second flow control valve 42 to control the flow rate of the second propellant stream 34 through the second conditioning conduit 22. Each flow control valve 40, 42 includes a mechanical stop to prevent the valve 40, 42 from being completely closed, and thereby maintain a degree of flow at all times through each of the first and second conditioning conduits 20, 22. Preferably the valves 40, 42 are also controlled to ensure adequate flow through the propellant conditioning assembly 10.

The propellant conditioning assembly 10 still further includes an output conduit 44 that receives the first and second propellant streams 26, 34 and merges them into a constant pressure propellant feed 46.

The output conduit 44 also includes an output temperature sensor 48 that is arranged to measure an output temperature $T_{OUT}$ of the merged propellant feed 46 in the output conduit 44.

In use, the relative proportion of the first and second propellant streams 26, 34 merging in the output conduit 44 is controlled to regulate the temperature of the merged constant pressure propellant feed 46 exiting from the output conduit 44.

More particularly, the input temperature $T_{IN}$ measured by the input temperature sensor 14 is firstly used to control the selective operation of the cooler and heater devices 24, 32. More particularly still, the cooler device 24 is operated to cool the first propellant stream 26 when the measured input temperature $T_{IN}$ is greater than a first temperature threshold, and the heater device 32 is operated to heat the second propellant stream 34 when the measured input temperature $T_{IN}$ is less than a second temperature threshold.

In the embodiment shown the first and second temperature thresholds differ from one another, although this need not necessarily be the case. By way of example, however, in the embodiment shown the first temperature threshold is 17° C. and the second temperature threshold is 15° C. Other temperature thresholds may however be used.

It follows that, in the embodiment shown, if the input temperature $T_{IN}$ of the propellant received from the propellant reservoir is greater than 17° C. then the cooler device 24, i.e. the first heat exchanger 28 and the associated cooler module 30, is operated to cool the first propellant stream 26 and similarly, if the input temperature $T_{IN}$ of the propellant received from the propellant reservoir is less than 15° C. then the heater device 32, i.e. the second heat exchanger 36 and the associated heater module 38, is operated to heat the second propellant stream 34. Meanwhile, if the input temperature $T_{IN}$ of the propellant lies within a 15° C. to 17° C. window then neither the cooler nor heater device 24, 32 is operated.

At the same time, the output temperature $T_{OUT}$ measured by the output temperature sensor 48 is used, in conjunction with the flow rate measured by the input flow rate sensor 14, to control the operation of the first and second flow control valves 40, 42.

More particularly, and by way of example only, the first flow control valve 40 is operated to increase the flow rate through the first conditioning conduit 20 and the second control valve 42 is operated to reduce the flow rate through the second conditioning conduit 22 when the measured output temperature $T_{OUT}$ is above a first output threshold, which preferably is the same as the first temperature threshold, i.e. preferably is 17° C. Similarly, the first control valve 40 is operated to reduce the flow rate through the first conditioning conduit 20 and the second control valve 42 is operated to increase the flow rate through the second conditioning conduit 22 when the measured output temperature $T_{OUT}$ is below a second output threshold, which preferably is the same as the second temperature threshold, i.e. preferably is 15° C.

In other embodiments of the invention, only one or other of the first and second flow control valves 40, 42 may be operated to change the flow rate through the corresponding conditioning conduit 20, 22 in response to the measured output temperature $T_{OUT}$ diverging from the first and second output thresholds, which may also differ from 17° C. and 15° C., respectively.

In the foregoing manner, adjustment of the first and/or second flow control valves 40, 42 to control the relative flow rates of different temperature first and second propellant streams 26, 34, provides fine control over the relative proportions of the different temperature first and second propellant streams 26, 34 that merge in the output conduit 44. Hence such adjustment similarly provides fine regulation of the temperature of the merged constant pressure propellant feed 46 in the output conduit 44.

A process plant according to a further embodiment of the invention is designated generally by reference numeral 100, as shown in FIG. 2.

The process plant 100 includes a propellant reservoir 102 in the form of a store tank 104, which can be resupplied with propellant from a supply tanker 106, via an off-loading pump 108. Other types of propellant reservoir, such as a buffer vessel (not shown) which may be resupplied from a supply cylinder via an off-loading pump, are also possible however.

The process plant 100 additionally includes a supply line 110 which extends from the propellant reservoir 102, i.e. the store tank 104, to the propellant conditioning assembly 10 shown in FIG. 1. The supply line 110 includes a constant pressure pump 112 to supply propellant at a constant pressure to the said propellant conditioning assembly 10.

The invention claimed is:

1. A propellant conditioning assembly, for providing a propellant feed to a medical dosing device filling apparatus, the assembly comprising:
   an input conduit to receive a propellant at a constant pressure from a propellant reservoir;
   a bifurcation to divide the input conduit into first and second conditioning conduits, the first conditioning conduit comprising a cooler device to selectively cool a diverted first propellant stream flowing through the first conditioning conduit, and the second conditioning conduit comprising a heater device to selectively heat a diverted second propellant stream flowing through the second conditioning conduit; and
   an output conduit to receive the first and second propellant streams, the relative proportion of the first and second propellant streams merging in the output conduit being controlled to regulate the temperature of a merged constant pressure propellant feed exiting from the output conduit,
   wherein the input conduit comprises an input temperature sensor arranged to measure an input temperature of the propellant in the input conduit, the measured input temperature being used to control the selective operation of the cooler and heater devices, wherein the first conditioning conduit comprises a first flow control valve to control the flow rate through the first conditioning conduit and the second conditioning conduit comprises a second flow control valve to control the flow rate through the second conditioning conduit, wherein the output conduit comprises an output temperature sensor arranged to measure an output temperature of the merged constant pressure propellant feed in the output conduit, the measured output temperature being used to control the operation of the first and second flow control valves, and wherein the input conduit comprises an input flow rate sensor to measure the flow rate of the propellant through the input conduit.

2. The propellant conditioning assembly of claim 1, wherein the heater device is operated to heat the second propellant stream flowing through the second conditioning conduit when the measured input temperature is less than a second temperature threshold.

3. The propellant conditioning assembly of claim 1, wherein each of the cooler device and the heater device comprises a heat exchanger.

4. The propellant conditioning assembly of claim 1, wherein the first flow control valve is operated to increase the flow rate through the first conditioning conduit or the second flow control valve is operated to reduce the flow rate through the second conditioning conduit when the measured output temperature is above a first output threshold, and the first flow control valve is operated to reduce the flow rate through the first conditioning conduit or the second flow control valve is operated to increase the flow rate through the second conditioning conduit when the measured output temperature is below a second output threshold.

5. A process plant, for providing a propellant feed to a medical device filling apparatus, comprising a propellant reservoir for a quantity of propellant, the propellant conditioning assembly of claim 1 and a supply line extending from the propellant reservoir to the propellant conditioning assembly, the supply line comprising a constant pressure pump to supply propellant at a constant pressure to the propellant conditioning assembly.

6. The propellant conditioning assembly of claim 1, wherein the cooler device is operated to cool the first propellant stream flowing through the first conditioning conduit when the measured input temperature is greater than a first temperature threshold.

7. The propellant conditioning assembly of claim 6, wherein the first and second temperature thresholds differ from one another.

8. A method of conditioning a propellant, for feeding to a medical dosing device filling apparatus, comprising the steps of:
(a) receiving in an output conduit a propellant at a constant pressure from a propellant reservoir;
(b) dividing the input conduit into first and second conditioning units, the first conditioning unit comprising a cooler device to selectively cool a diverted first propellant stream flowing through the first conditioning conduit, and the second conditioning conduit comprising a heater device to selectively heat a diverted second propellant stream flowing through the second conditioning conduit;
(c) receiving the first and second propellant streams in an output conduit;
(d) controlling the relative proportion of the first and second propellant streams merging in the output conduit to regulate the temperature of a merged constant pressure propellant feed exiting from the output conduit;
(e) using an input temperature sensor included in the input conduit to measure an input temperature of the propellant in the input conduit and using the measured input temperature to control the selective of the cooler and heater devices;
(f) using a first flow control valve included in the first conditioning unit to control the flow rate through the first conditioning unit and a second flow control valve included in the second conditioning unit to control the flow rate through the second conditioning unit;
(g) using an output temperature sensor included in the output conduit to measure an output temperature of the merged constant pressure propellant feed in the output conduit and using the measured output temperature to control the operation of the first and second flow control valves; and
(h) using an input flow rate sensor included in the input conduit to measure the flow rate of the propellant through the input conduit.

* * * * *